US008632536B2

(12) United States Patent
Kerr et al.

(10) Patent No.: US 8,632,536 B2
(45) Date of Patent: Jan. 21, 2014

(54) ELECTROSURGICAL PENCIL INCLUDING IMPROVED CONTROLS

(75) Inventors: Duane Kerr, Berthoud, CO (US); Monte Fry, Longmont, CO (US); Glenn A. Horner, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1276 days.

(21) Appl. No.: 12/144,356

(22) Filed: Jun. 23, 2008

(65) Prior Publication Data

US 2009/0248008 A1  Oct. 1, 2009

Related U.S. Application Data

(60) Provisional application No. 61/040,836, filed on Mar. 31, 2008.

(51) Int. Cl.
*A61B 18/18* (2006.01)

(52) U.S. Cl.
USPC .......................................................... 606/42

(58) Field of Classification Search
USPC .......................................... 604/22; 606/38, 42
See application file for complete search history.

(56) References Cited

U.S. PATENT DOCUMENTS

| 2,031,682 A | 2/1936 | Charles et al. |
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |

(Continued)

FOREIGN PATENT DOCUMENTS

| DE | 24 29 021 A1 | 1/1976 |
| DE | 24 60 481 A1 | 6/1976 |

(Continued)

OTHER PUBLICATIONS

International Search Report from Application No. EP 06 00 6908 dated Feb. 25, 2009.

(Continued)

*Primary Examiner* — Nicholas Lucchesi
*Assistant Examiner* — Jenna Zhang

(57) ABSTRACT

The present disclosure relates to electrosurgical devices having a plurality of hand-accessible variable controls. An electrosurgical device configured for connection to a source of electrosurgical energy is provided and includes a housing; an electrical circuit supported within the housing, the electrical circuit being connectable to the source of electrosurgical energy; and a controller slidably supported on the housing, wherein the controller is configured to exert a force on the electrical circuit to affect a change in the electrical circuit and to exert a force on a surface of the housing to provide a tactile feedback to a user of the electrosurgical device as the controller is moved relative to the housing.

13 Claims, 8 Drawing Sheets

(56) References Cited

U.S. PATENT DOCUMENTS

| | | |
|---|---|---|
| 3,902,494 A | 9/1975 | Haberlen et al. |
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,655,215 A * | 4/1987 | Pike ............ 606/42 |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,035,696 A | 7/1991 | Rydell |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,012 A | 1/1993 | Culp |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,366,464 A | 11/1994 | Belknap |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 A | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,496,314 A | 3/1996 | Eggers |
| 5,498,654 A | 3/1996 | Shimasaki et al. |

(56) References Cited

U.S. PATENT DOCUMENTS

| | | |
|---|---|---|
| D370,731 S | 6/1996 | Corace et al. |
| 5,531,722 A | 7/1996 | Van Hale |
| 5,549,604 A | 8/1996 | Sutcu et al. |
| 5,561,278 A | 10/1996 | Rutten |
| 5,601,224 A | 2/1997 | Bishop et al. |
| 5,609,573 A | 3/1997 | Sandock |
| 5,626,575 A | 5/1997 | Crenner |
| 5,630,417 A | 5/1997 | Petersen et al. |
| 5,630,426 A | 5/1997 | Eggers et al. |
| 5,630,812 A | 5/1997 | Ellman et al. |
| 5,633,578 A | 5/1997 | Eggers et al. |
| 5,634,912 A | 6/1997 | Injev |
| 5,634,935 A | 6/1997 | Taheri |
| 5,643,256 A | 7/1997 | Urueta |
| D384,148 S | 9/1997 | Monson |
| 5,669,907 A | 9/1997 | Platt, Jr. et al. |
| 5,674,219 A | 10/1997 | Monson et al. |
| 5,693,044 A | 12/1997 | Cosmescu |
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,712,543 A | 1/1998 | Sjostrom |
| 5,713,895 A | 2/1998 | Lontine et al. |
| 5,720,745 A | 2/1998 | Farin et al. |
| D393,067 S | 3/1998 | Geary et al. |
| 5,749,869 A | 5/1998 | Lindenmeier et al. |
| 5,765,418 A | 6/1998 | Rosenberg |
| 5,776,092 A | 7/1998 | Farin et al. |
| 5,788,688 A | 8/1998 | Bauer et al. |
| 5,797,907 A | 8/1998 | Clement |
| 5,800,431 A | 9/1998 | Brown |
| 5,836,897 A | 11/1998 | Sakurai et al. |
| 5,836,909 A | 11/1998 | Cosmescu |
| 5,836,944 A | 11/1998 | Cosmescu |
| D402,030 S | 12/1998 | Roberts et al. |
| D402,031 S | 12/1998 | Roberts et al. |
| 5,843,109 A | 12/1998 | Mehta et al. |
| 5,846,236 A | 12/1998 | Lindenmeier et al. |
| 5,859,527 A | 1/1999 | Cook |
| 5,868,768 A | 2/1999 | Wicherski et al. |
| 5,876,400 A | 3/1999 | Songer |
| 5,888,200 A | 3/1999 | Walen |
| 5,893,848 A | 4/1999 | Negus et al. |
| 5,893,849 A | 4/1999 | Weaver |
| 5,893,862 A | 4/1999 | Pratt et al. |
| 5,913,864 A | 6/1999 | Garito et al. |
| 5,919,219 A | 7/1999 | Knowlton |
| 5,928,159 A | 7/1999 | Eggers et al. |
| 5,938,589 A | 8/1999 | Wako et al. |
| 5,941,887 A | 8/1999 | Steen et al. |
| 5,944,737 A | 8/1999 | Tsonton et al. |
| 5,951,548 A | 9/1999 | DeSisto et al. |
| 5,951,581 A | 9/1999 | Saadat et al. |
| 5,954,686 A | 9/1999 | Garito et al. |
| 5,972,007 A | 10/1999 | Sheffield et al. |
| 6,004,318 A | 12/1999 | Garito et al. |
| 6,004,333 A | 12/1999 | Sheffield et al. |
| 6,004,335 A | 12/1999 | Vaitekunas et al. |
| 6,010,499 A | 1/2000 | Cobb |
| 6,022,347 A | 2/2000 | Lindenmeier et al. |
| 6,045,564 A | 4/2000 | Walen |
| 6,063,050 A | 5/2000 | Manna et al. |
| 6,068,603 A | 5/2000 | Suzuki |
| 6,068,627 A | 5/2000 | Orszulak et al. |
| 6,070,444 A | 6/2000 | Lontine et al. |
| 6,071,281 A | 6/2000 | Burnside et al. |
| 6,074,386 A | 6/2000 | Goble et al. |
| 6,074,387 A | 6/2000 | Heim et al. |
| 6,086,544 A | 7/2000 | Hibner et al. |
| 6,090,123 A | 7/2000 | Culp et al. |
| 6,099,525 A | 8/2000 | Cosmescu |
| 6,117,134 A | 9/2000 | Cunningham et al. |
| 6,139,547 A | 10/2000 | Lontine et al. |
| D433,752 S | 11/2000 | Saravia |
| 6,142,995 A | 11/2000 | Cosmescu |
| 6,146,353 A | 11/2000 | Platt, Jr. |
| 6,149,648 A | 11/2000 | Cosmescu |
| 6,156,035 A | 12/2000 | Songer |
| 6,197,024 B1 | 3/2001 | Sullivan |
| 6,200,311 B1 | 3/2001 | Danek et al. |
| D441,077 S | 4/2001 | Garito et al. |
| 6,213,999 B1 | 4/2001 | Platt, Jr. et al. |
| 6,214,003 B1 | 4/2001 | Morgan et al. |
| 6,238,388 B1 | 5/2001 | Ellman et al. |
| 6,241,723 B1 | 6/2001 | Heim et al. |
| 6,241,753 B1 | 6/2001 | Knowlton |
| 6,249,706 B1 | 6/2001 | Sobota et al. |
| 6,251,110 B1 | 6/2001 | Wampler |
| 6,257,241 B1 | 7/2001 | Wampler |
| 6,258,088 B1 | 7/2001 | Tzonev et al. |
| 6,273,862 B1 | 8/2001 | Privitera et al. |
| 6,277,083 B1 | 8/2001 | Eggers et al. |
| 6,286,512 B1 | 9/2001 | Loeb et al. |
| 6,287,305 B1 | 9/2001 | Heim et al. |
| 6,287,344 B1 | 9/2001 | Wampler et al. |
| 6,312,441 B1 | 11/2001 | Deng |
| 6,325,799 B1 | 12/2001 | Goble |
| 6,333,479 B1 | 12/2001 | Tai |
| D453,222 S | 1/2002 | Garito et al. |
| D453,833 S | 2/2002 | Hess |
| 6,350,276 B1 | 2/2002 | Knowlton |
| 6,352,544 B1 | 3/2002 | Spitz |
| 6,355,034 B2 | 3/2002 | Cosmescu |
| 6,358,281 B1 | 3/2002 | Berrang et al. |
| 6,361,532 B1 | 3/2002 | Burek |
| D457,955 S | 5/2002 | Bilitz |
| 6,386,032 B1 | 5/2002 | Lemkin et al. |
| 6,395,001 B1 | 5/2002 | Ellman et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,725 B1 | 6/2002 | Khandkar et al. |
| 6,413,255 B1 | 7/2002 | Stern |
| 6,416,491 B1 | 7/2002 | Edwards et al. |
| 6,416,509 B1 | 7/2002 | Goble et al. |
| 6,425,912 B1 | 7/2002 | Knowlton |
| 6,458,122 B1 | 10/2002 | Pozzato |
| 6,458,125 B1 | 10/2002 | Cosmescu |
| 6,461,352 B2 | 10/2002 | Morgan et al. |
| 6,464,698 B1 | 10/2002 | Falwell |
| 6,464,702 B2 | 10/2002 | Schulze et al. |
| 6,471,659 B2 | 10/2002 | Eggers et al. |
| 6,494,882 B1 | 12/2002 | Lebouitz et al. |
| 6,500,169 B1 | 12/2002 | Deng |
| 6,511,479 B2 | 1/2003 | Gentelia et al. |
| 6,526,320 B2 | 2/2003 | Mitchell |
| 6,551,313 B1 | 4/2003 | Levin |
| 6,558,383 B2 | 5/2003 | Cunningham et al. |
| 6,585,664 B2 | 7/2003 | Burdorff et al. |
| 6,589,239 B2 | 7/2003 | Khandkar et al. |
| 6,610,054 B1 | 8/2003 | Edwards et al. |
| 6,610,057 B1 | 8/2003 | Ellman et al. |
| 6,616,658 B2 | 9/2003 | Ineson |
| 6,618,626 B2 | 9/2003 | West, Jr. et al. |
| 6,620,161 B2 | 9/2003 | Schulze et al. |
| 6,632,193 B1 | 10/2003 | Davison et al. |
| 6,652,514 B2 * | 11/2003 | Ellman et al. ............ 606/37 |
| 6,662,053 B2 | 12/2003 | Borkan |
| 6,669,691 B1 | 12/2003 | Taimisto |
| 6,685,701 B2 | 2/2004 | Orszulak et al. |
| 6,685,704 B2 | 2/2004 | Greep |
| 6,702,812 B2 | 3/2004 | Cosmescu |
| 6,710,546 B2 | 3/2004 | Crenshaw |
| 6,712,813 B2 | 3/2004 | Ellman et al. |
| 6,719,746 B2 | 4/2004 | Blanco |
| 6,740,079 B1 | 5/2004 | Eggers et al. |
| 6,747,218 B2 | 6/2004 | Huseman et al. |

(56) References Cited

U.S. PATENT DOCUMENTS

| | | |
|---|---|---|
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 6,794,929 B2 | 9/2004 | Pelly |
| 6,830,569 B2 | 12/2004 | Thompson et al. |
| 6,840,948 B2 | 1/2005 | Albrecht et al. |
| 6,855,140 B2 | 2/2005 | Albrecht et al. |
| 6,902,536 B2 | 6/2005 | Manna et al. |
| 6,905,496 B1 | 6/2005 | Ellman et al. |
| 6,923,804 B2 | 8/2005 | Eggers et al. |
| 6,923,809 B2 | 8/2005 | Eggers et al. |
| 6,939,347 B2 | 9/2005 | Thompson |
| 6,955,674 B2 | 10/2005 | Eick et al. |
| D515,412 S | 2/2006 | Waaler et al. |
| 7,033,353 B2 | 4/2006 | Stoddard et al. |
| D521,641 S | 5/2006 | Reschke et al. |
| D535,396 S | 1/2007 | Reschke et al. |
| 7,156,842 B2 | 1/2007 | Sartor et al. |
| 7,156,844 B2 | 1/2007 | Reschke et al. |
| 7,235,072 B2 | 6/2007 | Sartor et al. |
| 7,241,294 B2 | 7/2007 | Reschke |
| 7,244,257 B2 | 7/2007 | Podhajsky et al. |
| 7,393,354 B2 | 7/2008 | Buchman, II et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087179 A1 | 7/2002 | Culp et al. |
| 2002/0095199 A1 | 7/2002 | West, Jr. et al. |
| 2002/0103485 A1 | 8/2002 | Melnyk et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0061661 A1 | 4/2003 | Borders et al. |
| 2003/0065321 A1* | 4/2003 | Carmel et al. .................. 606/41 |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 | 2/2004 | Yamaki et al. |
| 2004/0034346 A1 | 2/2004 | Stern et al. |
| 2004/0054370 A1 | 3/2004 | Given |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0236323 A1 | 11/2004 | Schoenman et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0113817 A1 | 5/2005 | Isaacson et al. |
| 2005/0113818 A1 | 5/2005 | Sartor et al. |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0041257 A1 | 2/2006 | Sartor et al. |
| 2006/0058783 A1 | 3/2006 | Buchman |
| 2006/0178667 A1* | 8/2006 | Sartor et al. .................. 606/42 |
| 2007/0049926 A1 | 3/2007 | Sartor |
| 2007/0093810 A1 | 4/2007 | Sartor |
| 2007/0142832 A1 | 6/2007 | Sartor |
| 2007/0260238 A1 | 11/2007 | Guerra |
| 2007/0260239 A1 | 11/2007 | Podhajsky et al. |
| 2007/0260240 A1 | 11/2007 | Rusin |
| 2009/0187188 A1 | 7/2009 | Guerra |

FOREIGN PATENT DOCUMENTS

| | | |
|---|---|---|
| DE | 30 45 996 | 7/1982 |
| EP | 0186369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1656900 | 5/2006 |
| EP | 1645234 | 12/2006 |
| EP | 1852078 | 11/2007 |
| EP | 1852078 A | 11/2007 |
| FR | 2235669 | 1/1975 |
| FR | 2798579 | 3/2001 |
| GB | 2257831 A | 1/1993 |
| WO | WO 94/20032 | 9/1994 |
| WO | WO 96/39086 | 12/1996 |
| WO | WO 98/43264 | 10/1998 |
| WO | WO 01/39681 A | 6/2001 |
| WO | WO 01/64122 | 9/2001 |
| WO | WO 2002/47568 A1 | 6/2002 |
| WO | WO 2004/010883 A1 | 2/2004 |

(56) References Cited

FOREIGN PATENT DOCUMENTS

| WO | WO 2004/045436 A1 | 6/2004 |
|----|----|----|
| WO | WO 2004/073753 A2 | 9/2004 |
| WO | WO 2005/060849 | 7/2005 |

OTHER PUBLICATIONS

International Search Report from Application No. EP 08 02 1070 dated Apr. 1, 2009.
Zucker, Karl, Surgical Laparoscopy, Lippincott Williams & Wilkins, Ed. 2, 2001 (2 pages).
International Search Report from PCT-US03-37111; Jul. 21, 2004.
International Search Report from PCT-US04-04685; Aug. 6, 2004.
International Search Report from EP-0401-5980; Sep. 30, 2004.
International Search Report from PCT-US03-22900; Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.
International Search Report mailed Sep. 21, 2009 in International Application No. PCT/US2009/038980.

\* cited by examiner

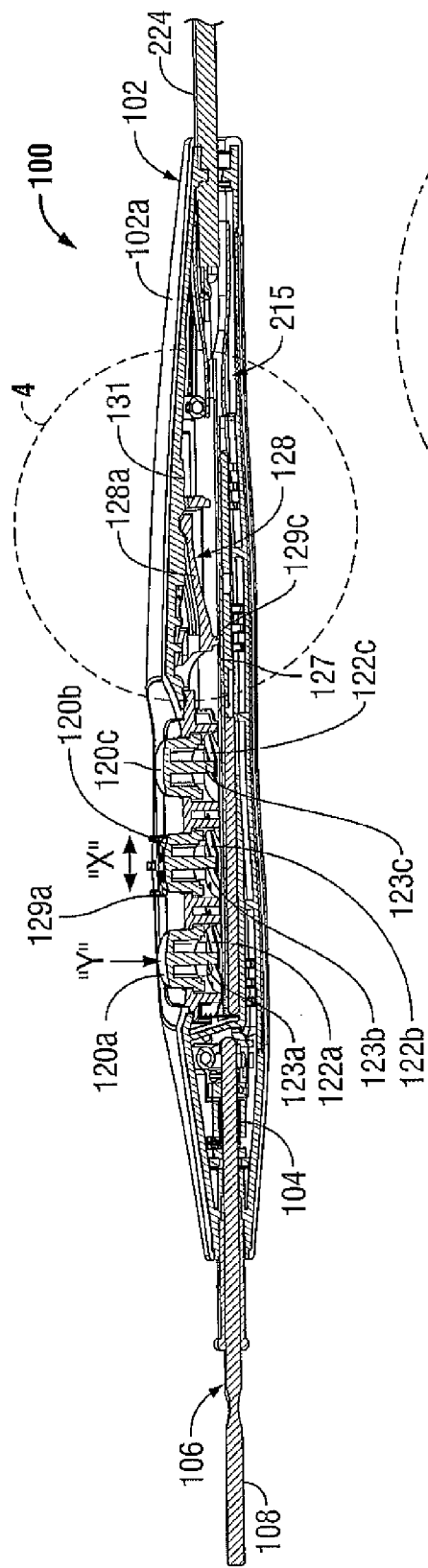
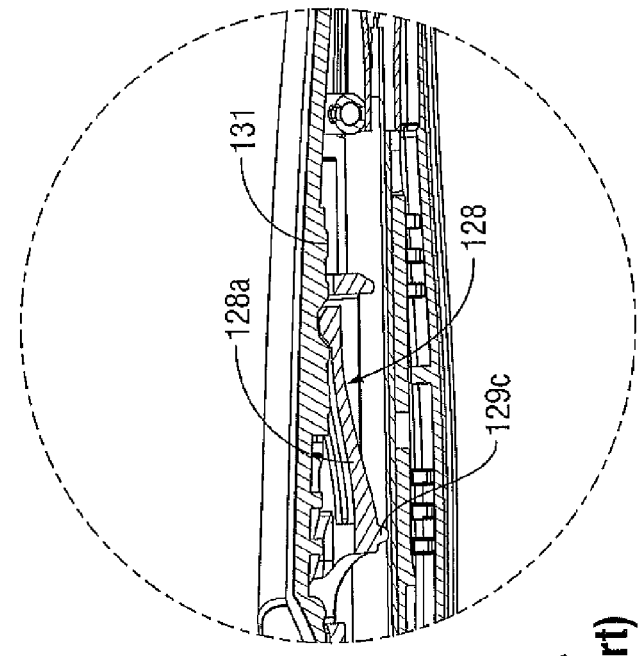
FIG. 3
(Prior Art)
FIG. 4
(Prior Art)

ELECTROSURGICAL PENCIL INCLUDING IMPROVED CONTROLS

CROSS-REFERENCE TO RELATED APPLICATION

The present application claims the benefit of and priority to U.S. Provisional Application Ser. No. 61/040,836, filed on Mar. 31, 2008, the entire content of which is incorporated herein by reference.

BACKGROUND

1. Technical Field

The present disclosure relates generally to electrosurgical instruments and, more particularly, to an electrosurgical pencil having a plurality of hand-accessible variable controls.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

As used herein the term "electrosurgical pencil" is intended to include instruments which have a handpiece which is attached to an active electrode and which is used to cauterize, coagulate and/or cut tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect.

The power or energy parameters are typically controlled from outside the sterile field which requires an intermediary like a circulating nurse to make such adjustment.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. However, so many options also tend to complicate simple surgical procedures and may lead to confusion. Moreover, surgeons typically follow preset control parameters and stay within known modes and power settings. Therefore, there exists a need to allow the surgeon to selectively control and easily select and regulate the various modes and power settings utilizing simple and ergonomically friendly controls associated with the electrosurgical pencil.

Existing electrosurgical instrument systems allow the surgeon to change between two pre-configured settings (i.e., coagulation and cutting) via two discrete switches disposed on the electrosurgical pencil itself. Other electrosurgical instrument systems allow the surgeon to increment the power applied when the coagulating or cutting switch of the instrument is depressed by adjusting or closing a switch on the electrosurgical generator. The surgeon then needs to visually verify the change in the power being applied by looking at various displays and/or meters on the electrosurgical generator. In other words, all of the adjustments to the electrosurgical instrument and parameters being monitored during the use of the electrosurgical instrument are typically located on the electrosurgical generator. As such, the surgeon must continually monitor the electrosurgical generator during the surgical procedure. Furthermore, someone outside the sterile field must continually adjust the parameters of the electrical instrument, which prolongs the duration of the procedure.

Accordingly, the need exists for electrosurgical instruments which do not require the surgeon to continually monitor the electrosurgical generator during the surgical procedure. Further, a need exists for electrosurgical instruments, which permit the surgeon to accurately self-adjust the electrical parameters of the instrument from within the sterile field. In addition, the need exists for electrosurgical instruments which may be configured such that the power output can be adjusted without the surgeon having to turn his/her vision away from the operating site and toward the electrosurgical generator.

SUMMARY

The present disclosure relates to electrosurgical pencils having a plurality of hand-accessible variable controls.

According to an aspect of the present disclosure, an electrosurgical pencil is provided including an elongated housing configured to support an electrocautery electrode extending distally therefrom; at least one voltage divider network supported on the housing, the at least one voltage divider network operable to electrically connect to a source of electrosurgical energy for controlling at least one of an intensity and a mode of electrosurgical energy being delivered to the electrocautery electrode; and an intensity controller slidably supported on the housing. The intensity controller is configured to exert a force on the at least one voltage divider network and to provide a tactile feedback to a user of the electrosurgical pencil as the intensity controller is moved relative to the housing.

The intensity controller may include a nub extending from a surface thereof. The nub may be configured to contact the at least one voltage divider network and affect the at least one voltage divider network as the intensity controller is moved relative to the housing.

The intensity controller may include a spring plunger assembly configured to operatively engage a tactile feature formed in the housing. The spring plunger assembly may include a stem and a biasing member. The stem may be disposed on a side opposite to the nub and is configured to retain an actuator.

The biasing member may be configured to maintain the actuator in contact with the tactile feature formed in the housing. The actuator may be disposed at one of a distal, a proximal and a substantially aligned location with respect to the nub.

The intensity controller may include a spring lever assembly configured to operatively engage a tactile feature formed in the housing. The spring lever assembly may include a lever and a biasing member for maintaining the lever in contact with the tactile feature. The lever may be pivotally connected to a body portion of the intensity controller, on a side opposite to the nub.

The biasing member may be a spring.

A tip of the lever may be disposed at one of a distal, a proximal and a substantially aligned location with respect to the nub.

According to another aspect of the present disclosure, an electrosurgical device configured for connection to a source of electrosurgical energy is provided. The electrosurgical device includes a housing; an electrical circuit supported within the housing, the electrical circuit being connectable to the source of electrosurgical energy; and a controller slidably supported on the housing, wherein the controller is configured to exert a force on the electrical circuit to affect a change in the electrical circuit and to provide a tactile feedback to a user of the electrosurgical device as the controller is moved relative to the housing.

The controller may include a nub extending from a surface thereof and being dimensioned to contact the electrical circuit. The electrical circuit may be a voltage divider network capable of controlling at least one of an intensity and a mode of electrosurgical energy being delivered, and wherein the nub is configured to contact the voltage divider network and affect a change in at least one of the intensity and the mode of electrosurgical energy being delivered as the controller is moved relative to the housing.

The controller may include a spring plunger assembly configured to operatively engage a tactile feature formed in the housing. The spring plunger assembly may include a stem and a biasing member. The stem may be disposed on a side opposite to the nub and is configured to retain an actuator. The biasing member may be configured to maintain the actuator in contact with the tactile feature formed in the housing. The actuator may be disposed at one of a distal, a proximal and a substantially aligned location with respect to the nub.

The controller may include a spring lever assembly configured to operatively engage a tactile feature formed in the housing. The spring lever assembly may include a lever and a biasing member for maintaining the lever in contact with the tactile feature. The lever may be pivotally connected to a body portion of the intensity controller, on a side opposite to the nub. The biasing member may be a spring.

A tip of the lever may be disposed at one of a distal, a proximal and a substantially aligned location with respect to the nub.

According to a further aspect of the present disclosure, an electrosurgical pencil is provided including an elongated housing configured to support an electrocautery electrode extending distally therefrom; at least one voltage divider network supported on the housing, the at least one voltage divider network operable to electrically connect to the source of electrosurgical energy for controlling at least one of an intensity and a mode of electrosurgical energy being delivered to the electrocautery electrode; and an intensity controller slidably supported on the housing, wherein the intensity controller is configured to exert a force on the at least one voltage divider network and provide a tactile feedback to a user of the electrosurgical pencil as the intensity controller is moved relative to the housing.

The intensity controller may include a lever pivotally connected to a body portion thereof and contactable with the housing and the at least one voltage divider network. The lever may include a first end configured for engagement with a tactile feature formed in the housing. The lever may include a second end configured for engagement with the at least one voltage divider network.

The intensity controller may include a biasing member configured to maintain a first end of the lever in contact with the tactile feature formed in the housing. The intensity controller may include a biasing member configured to maintain a second end of the lever in contact with the at least one voltage divider network. The intensity controller may include a biasing member configured to maintain a first end of the lever in contact with the tactile feature formed in the housing and to maintain a second end of the lever in contact with the at least one voltage divider network.

The biasing members may be one of a coil spring, a tension spring and a compression spring. The tactile feature may include one or more adjacent detents. In use, movement of the first end of the lever into the one or more adjacent detents may cause the second end of the lever to substantially strike the at least one voltage divider network.

According to yet another aspect of the present disclosure, an electrosurgical device configured for connection to a source of electrosurgical energy is provided. The electrosurgical device includes a housing; an electrical circuit supported within the housing, the electrical circuit being connectable to the source of electrosurgical energy; and a controller slidably supported on the housing, wherein the controller is configured to exert a force on the electrical circuit to affect a change in the electrical circuit and to exert a force on a surface of the housing to provide a tactile feedback to a user of the electrosurgical device as the controller is moved relative to the housing.

The electrical circuit may comprise at least one voltage divider network capable of controlling at least one of an intensity and a mode of electrosurgical energy being delivered, and wherein the controller may include a lever pivotally connected to a body portion thereof and contactable with the housing and the at least one voltage divider network.

The lever may include a first end configured for engagement with a tactile feature formed in the housing. The lever may include a second end configured for engagement with the at least one voltage divider network.

The controller may include a biasing member configured to maintain a first end of the lever in contact with the tactile feature formed in the housing. The controller may include a biasing member configured to maintain a second end of the lever in contact with the at least one voltage divider network. The controller may include a biasing member configured to maintain a first end of the lever in contact with the tactile feature formed in the housing and to maintain a second end of the lever in contact with the at least one voltage divider network. The biasing members may be one of a coil spring, a tension spring and a compression spring.

The tactile feature may include one or more adjacent detents.

In use, movement of the first end of the lever into the one or more adjacent detents may cause the second end of the lever to substantially strike the at least one voltage divider network.

According to still another aspect of the present disclosure, an electrosurgical pencil is provided including an elongated housing configured to support an electrocautery electrode extending distally therefrom; at least one voltage divider network supported on the housing, the at least one voltage divider network operable to electrically connect to the source of electrosurgical energy for controlling at least one of an intensity and a mode of electrosurgical energy being delivered to the electrocautery electrode, wherein the at least one voltage divider network defines a plurality of tactile enhancement features; and an intensity controller slidably supported on the housing, wherein the intensity controller is configured to exert a force on the at least one voltage divider network and engage the tactile enhancement feature and provide a tactile feedback to a user of the electrosurgical pencil as the intensity controller is moved relative to the housing.

The electrosurgical pencil may further include a tactile mask overlying at least a portion of the at least one voltage divider network, wherein the tactile mask defines the plurality of tactile enhancement regions. The tactile enhancement features of the tactile mask may include at least one aperture formed therein.

The intensity controller may include a tactile feedback transmitting feature configured to project through the at least one aperture formed in the tactile mask to selectively engage the at least one voltage divider network. The tactile feedback transmitting feature may include at least one of an actuator and a nub selectively positionable within the aperture of the tactile mask.

At least one of an actuator and a nub may extend from a surface of the intensity controller, in a direction toward the tactile mask.

The tactile feedback transmitting feature may further comprise a spring plunger assembly including a biasing member for maintaining the tactile feedback transmitting feature in contact with at least one of the voltage divider network and the tactile mask.

The tactile feedback transmitting feature may be configured to selectively strike the at least one voltage divider network.

According to yet another aspect of the present disclosure, an electrosurgical device, configured for connection to a source of electrosurgical energy, is provided. The electrosurgical device comprises a housing; an electrical circuit supported within the housing, the electrical circuit being connectable to the source of electrosurgical energy, wherein the electrical circuit is provided with at least one tactile enhancement feature; and a controller slidably supported on the housing, wherein the controller is configured to exert a force on the electrical circuit to affect a change in the electrical circuit and to exert a force on a surface of the housing to engage the tactile enhancement feature and provide a tactile feedback to a user of the electrosurgical device as the controller is moved relative to the housing.

The electrosurgical device may further include a tactile mask overlying at least a portion of electrical circuit, wherein the tactile mask defines the plurality of tactile enhancement regions.

The tactile enhancement features of the tactile mask may include at least one aperture formed therein.

The controller may include a tactile feedback transmitting feature configured to project through the at least one aperture formed in the tactile mask to selectively engage the electrical circuit. The tactile feedback transmitting feature may include at least one of an actuator and a nub selectively positionable within the aperture of the tactile mask. At least one of an actuator and a nub may extend from a surface of the controller, in a direction toward the tactile mask.

The tactile feedback transmitting feature may further include a spring plunger assembly including a biasing member for maintaining the tactile feedback transmitting feature in contact with at least one of the electrical circuit and the tactile mask.

The tactile feedback transmitting feature may be configured to selectively strike the electrical circuit.

The electrical circuit may include at least one voltage divider network.

According to still another aspect of the present disclosure, an electrosurgical pencil is provided including an elongated housing configured to support an electrocautery electrode extending distally therefrom; at least one voltage divider network supported on the housing, the at least one voltage divider network operable to electrically connect to the source of electrosurgical energy for controlling at least one of an intensity and a mode of electrosurgical energy being delivered to the electrocautery electrode; and an intensity controller slidably supported on the housing, wherein the intensity controller is configured to exert a force on each of the housing and the at least one voltage divider network, wherein the intensity controller provides a tactile feedback to a user of the electrosurgical pencil as the intensity controller is moved relative to the housing.

The intensity controller may include a torsion spring pivotally supported on a body portion thereof, wherein the torsion spring is in contact with at least one of the housing and the electrical circuit. The torsion spring may include a first leg configured for engagement with a tactile feature formed in the housing. The torsion spring may include a second leg configured for engagement with the at least one voltage divider network.

The torsion spring may include a first leg configured for engagement with a tactile feature formed in the housing and a second leg configured for engagement with the at least one voltage divider network.

The intensity controller may include a link assembly pivotally supported on a body portion. The link assembly may include a first leg configured for engagement with a tactile feature formed in the housing; and a second leg configured for engagement with the at least one voltage divider network.

The link assembly may further include a biasing member interposed between the first leg and the second leg for maintaining the first leg in engagement with the tactile feature formed in the housing and for maintaining the second leg in engagement with the at least one voltage divider network.

The biasing member may be configured for maintaining the first leg in engagement with the tactile feature formed in the housing. The biasing member may be configured for maintaining the second leg in engagement with the at least one voltage divider network.

According to still another aspect of the present disclosure, an electrosurgical device, configured for connection to a source of electrosurgical energy, is provided. The electrosurgical device comprises a housing; an electrical circuit supported within the housing, the electrical circuit being connectable to the source of electrosurgical energy; and a controller slidably supported on the housing, wherein the controller is configured to exert a force on each of the housing and the electrical circuit to affect a change in the electrical circuit and to provide a tactile feedback to a user of the electrosurgical device as the controller is moved relative to the housing.

The controller may include a torsion spring pivotally supported on a body portion thereof, wherein the torsion spring is in contact with at least one of the housing and the electrical circuit. The torsion spring may include a first leg configured for engagement with a tactile feature formed in the housing. The torsion spring may include a second leg configured for engagement with the electrical circuit. The torsion spring may include a first leg configured for engagement with a tactile feature formed in the housing and a second leg configured for engagement with the electrical circuit.

The controller may include a link assembly pivotally supported on a body portion. The link assembly may include a first leg configured for engagement with a tactile feature formed in the housing; and a second leg configured for engagement with the electrical circuit. The link assembly may further include a biasing member interposed between the first leg and the second leg for maintaining the first leg in engagement with the tactile feature formed in the housing and for maintaining the second leg in engagement with the electrical circuit. The biasing member may be configured for maintaining the first leg in engagement with the tactile feature formed in the housing. The biasing member may be configured for maintaining the second leg in engagement with the electrical circuit.

The electrical circuit may include at least one voltage divider network supported on the housing, the at least one voltage divider network operable to electrically connect to the source of electrosurgical energy for controlling at least one of an intensity and a mode of electrosurgical energy being delivered to the electrocautery electrode.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

FIG. 3 is a longitudinal, cross-sectional, side elevational view of the electrosurgical pencil of FIGS. 1 and 2;

FIG. 4 is an enlarged view of the indicated area of detail of FIG. 3;

DETAILED DESCRIPTION

Figure 1:
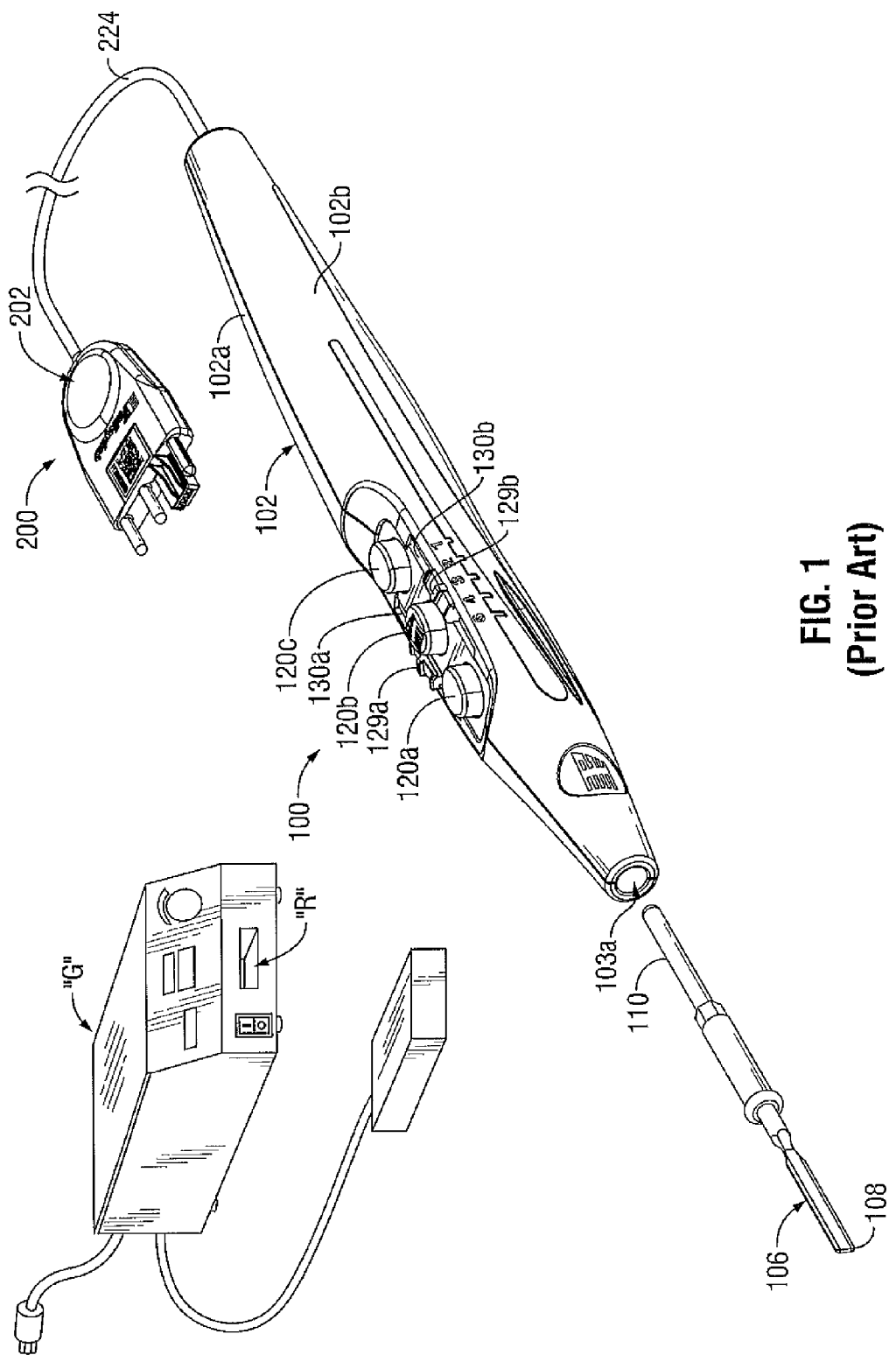
FIG. 1 is a perspective view of a prior art electrosurgical system including an electrosurgical generator and an electrosurgical pencil.

Preferred embodiments of the presently disclosed electrosurgical pencil will now be described in detail with reference to the drawing figures wherein like reference numerals identify similar or identical elements. As used herein, the term "distal" refers to that portion which is further from the user while the term "proximal" refers to that portion which is closer to the user or surgeon.

FIG. 1 sets forth a perspective view of an electrosurgical system including an electrosurgical pencil 100 constructed in accordance with a prior art embodiment. While the following description will be directed towards electrosurgical pencils it is envisioned that the features and concepts (or portions thereof) of the present disclosure can be applied to any electrosurgical type instrument, e.g., forceps, suction coagulators, vessel sealers, wands, etc.

Figure 2:
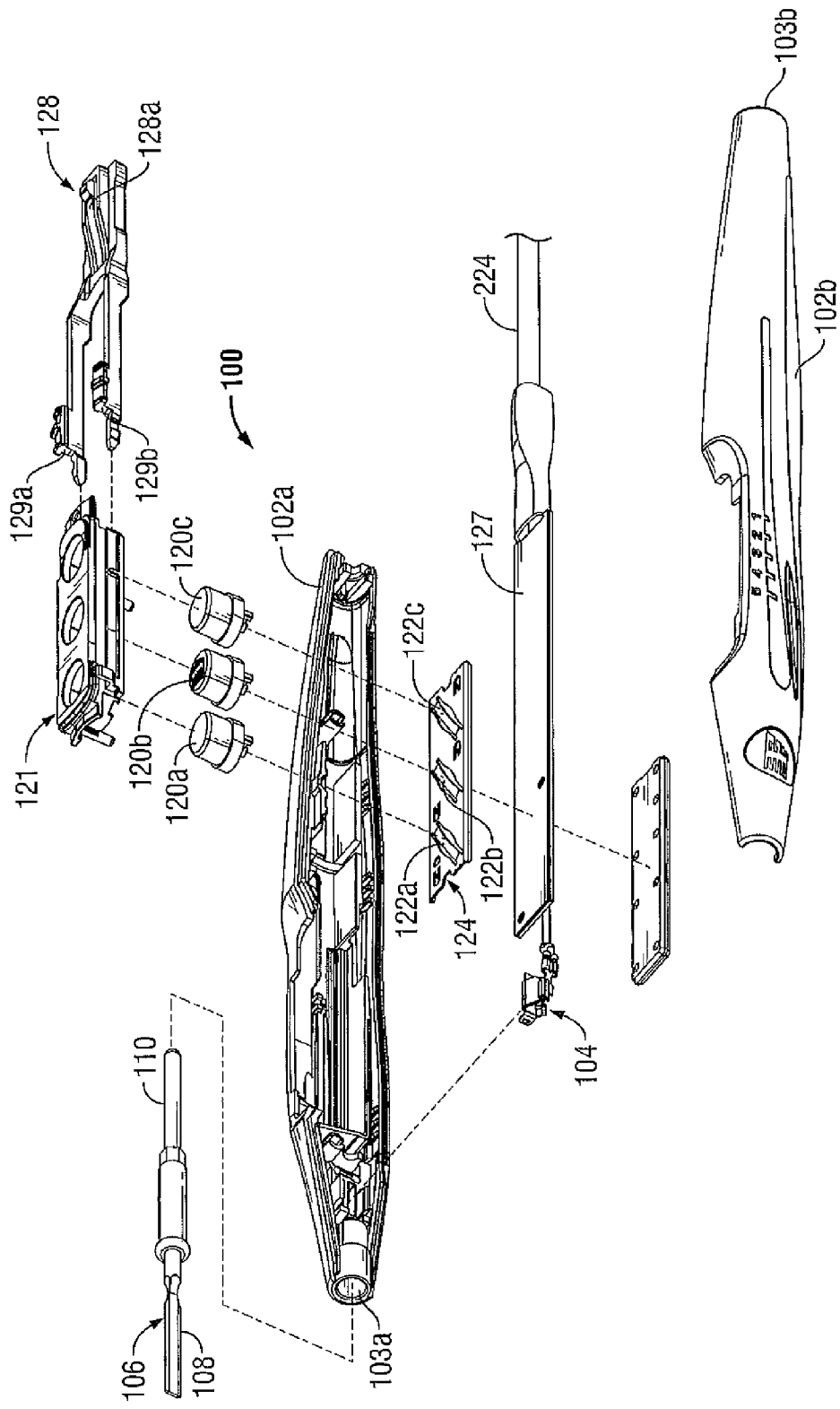
FIG. 2 is an exploded perspective view of the electrosurgical pencil of FIG. 1.

As seen in FIGS. 1-5, electrosurgical pencil 100 includes an elongated housing 102 having a right-half shell section 102a and a left-half shell section 102b. As seen in FIGS. 1 and 2, when right and left-half shell sections 102a, 102b are connected to one another, a distal opening 103a is defined therebetween, through which an electrode 106 extends, and a proximal opening 103b (see FIG. 2) is defined therebetween, through which connecting cable 224 (see FIG. 1) extends. As seen in FIG. 1, electrosurgical pencil 100 is coupled to an electrosurgical generator "G" via a plug assembly 200 connected to connecting cable 224.

As seen in FIG. 2, electrosurgical pencil 100 further includes an electrode receptacle 104 disposed at a distal end of housing 102, and a replaceable electrode 106 operatively and removably connectable to electrode receptacle 104.

With continued reference to FIGS. 1-3, electrosurgical pencil 100 includes three activation buttons 120a-120c, each of which is reciprocally supported in a carrier 121 (see FIG. 2) of a controller unit which is supported in housing 102. Each activation button 120a-120c includes a portion which extends through an upper surface of housing 102.

As seen in FIGS. 2 and 3, each activation button 120a-120c is operatively supported on a respective tactile element 122a-122c formed in a switch plate 124.

Each activation button 120a-120c controls the transmission of RF electrical energy supplied from generator "G" to electrode 106. Switch plate 124 is positioned over the top of a voltage divider network 127 (hereinafter "VDN 127") such that tactile elements 122a-122c are in operative association therewith.

As seen in FIGS. 1-4, electrosurgical pencil 100 includes an intensity controller 128 slidingly supported in housing 102. Intensity controller 128 includes a pair of nubs 129a, 129b which are slidingly supported, one each, in respective guide channels 130a, 130b (see FIG. 1).

Figure 5:
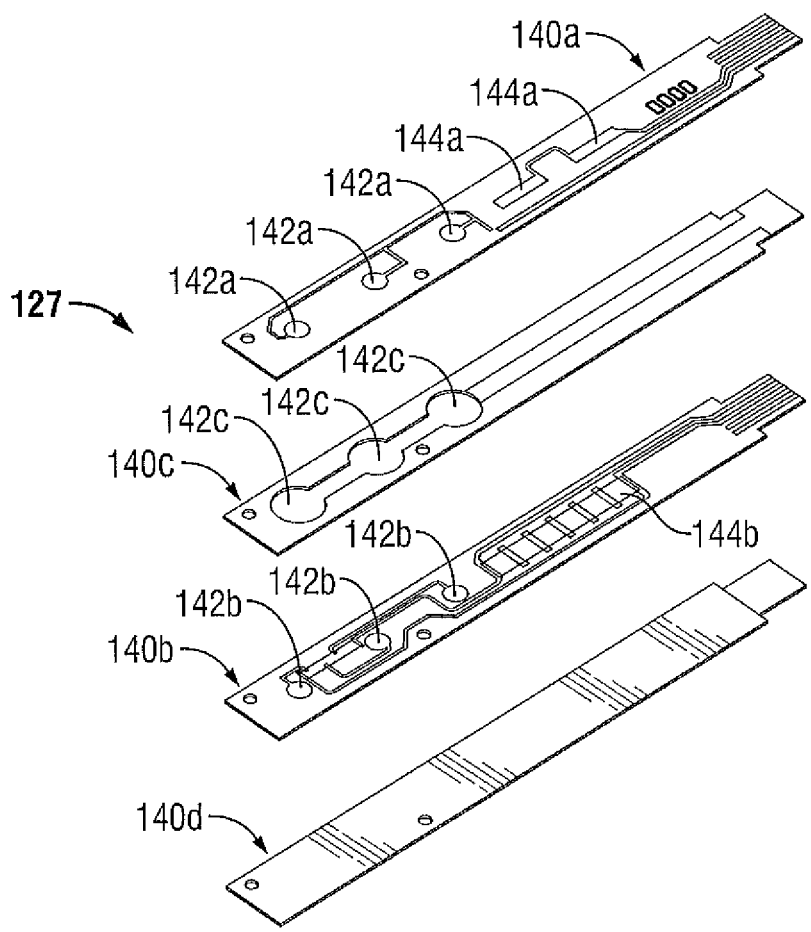
FIG. 5 is an exploded perspective view of a voltage divider network.

As seen in FIGS. 3 and 4, intensity controller 128 includes a third nub 129c extending from a bottom surface thereof which contacts and presses into or against VDN 127. As seen in FIG. 5, VDN 127 includes electrical contacts 144a provided on upper layer 140a and resistive element 144b on lower layer 140b. In this manner, as intensity controller 128 is displaced in a distal and proximal direction relative to housing 102, third nub 129c moves along VDN 127, thereby pressing electrical contact 144a from upper layer 140a of VDN 127 against resistance element 144b of lower layer 140b of VDN 127. In so doing, a resistance value of resistance element 144b is changed thereby changing the value of the voltage measured by electrosurgical generator "G". The electrosurgical generator "G" in turn varies the intensity of the waveform being transmitted to electrode 106.

Slidable manipulation or movement of intensity controller 128 adjusts the power parameters (e.g., voltage, power and/or current intensity) and/or the power verses impedance curve shape to affect the output intensity of the waveform.

In order to vary the intensity of the power parameters of electrosurgical pencil 100, the surgeon displaces intensity controller 128, by manipulating at least one of nubs 129a, 129b, in either of the directions indicated by double-headed arrow "X" (see FIG. 3).

Intensity controller 128 is also operable to provide a degree of tactile feedback by the inter-engagement of resilient finger 128a of intensity controller 128 in detents 131 formed along an inner surface of right-half shell section 102a (see FIGS. 3 and 4).

As seen in FIG. 5, VDN 127 includes a pair of layers 140a, 140b of resilient material each supporting a plurality of electrical contacts 142a, 142b thereon. Electrical contacts 142a from an upper layer 140a of VDN 127 are in juxtaposed electrical relation with respect to electrical contacts 142b from a lower layer 140b of VDN 127. The electrical contacts 142a, 142b of the upper and the lower layers 140a, 140b of VDN 127 are in juxtaposed relation with respective tactile elements 122a-122c.

Upper and lower layers 140a, 140b of VDN 127 are separated by a dividing layer 140c. Dividing layer 140c includes a first series of apertures 142c formed therein which are in vertical registration with electrical contacts 142a, 142b. Dividing layer 140c includes a second aperture 144c formed therein which is in vertical registration between electrical contacts 144a provided on upper layer 140a and a variable resistance element 144d provided on lower layer 140b. Upper layer 140a, lower layer 140b, and dividing layer 140c are supported on a support layer 140d.

In operation, and depending on the particular electrosurgical function desired, the surgeon depresses one of activation buttons 120a-120c, in the direction indicated by arrow "Y" (see FIG. 3) thereby urging and/or deflecting a corresponding tactile element 122a-122c against VDN 127 and thereby causing the respective electrical contact 142a of upper layer 140a to electrically engage the respective electrical contact 142b of the lower layer 140b. In so doing, a respective characteristic voltage is generated and measured by electrosurgical generator "G". In turn, depending on the characteristic voltage generated, generator "C" selects and transmits an appropriate waveform output to electrocautery blade 106.

Reference may be made to U.S. application Ser. No. 11/337,990 filed on Jan. 24, 2006, the entire content of which is incorporated herein by reference, for a more detailed discussion of the construction and operation of electrosurgical pencil 100.

Turning now to FIGS. 6A-6D, a series of sliders or intensity controllers 228 according to an embodiment of the present disclosure is shown. Sliders 228 are configured to increase a contact force exerted on VDN 127 while maintaining a degree of facility for an end user to move slider 228 relative to housing 102 of electrosurgical pencil 100.

Figure 6A:
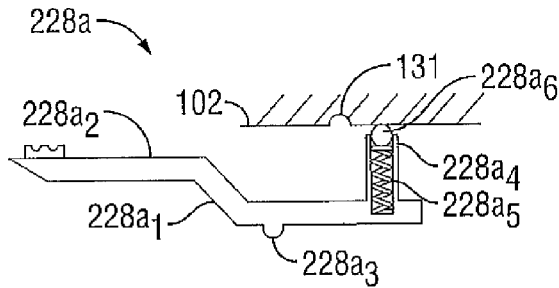
FIG. 6A is a schematic side elevational view of a slider according to an embodiment of the present disclosure, for use in an electrosurgical pencil as shown in FIGS. 1-4.

As seen in FIG. 6A, a slider 228a may include a body portion $228a_1$ and at least one arm $228a_2$ extending from body portion $228a_1$ and configured for slidable engagement in guide channels 130a, 130b (see FIG. 1) of electrosurgical pencil 100. Slider 228a includes a nub $228a_3$ extending or projecting from a bottom surface thereof, such as, for example, from a bottom surface of body portion $228a_1$. Slider 228a further includes a spring plunger assembly having a stem $228a_4$ extending from body portion $228a_1$, on a side opposite nub $228a_3$, and defining a recess configured to retain a biasing member $228a_5$ and an actuator $228a_6$ therein. The spring plunger assembly is located distal or proximal of nub $228a_3$.

In use, as slider 228a is moved distally and proximally relative to housing 102 of electrosurgical pencil 100, nub $228a_3$ moves along VDN 127 thereby affecting VDN 127 while actuator $228a_6$ of the spring plunger assembly inter-engages with detents or tactile features 131 formed in housing 102 of electrosurgical pencil 100 to thereby provide a degree of tactile feedback to the user of electrosurgical pencil 100. Biasing member $228a_5$ functions to maintain nub $228a_3$ in contact with VDN 127 and actuator $228a_6$ of the spring plunger assembly in contact with detents or tactile features 131 formed in housing 102 of electrosurgical pencil 100.

Figure 6B:
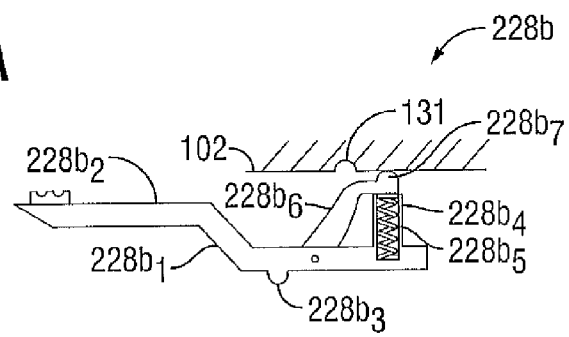
FIG. 6B is a schematic side elevational view of a slider according to another embodiment of the present disclosure, for use in an electrosurgical pencil as shown in FIGS. 1-4.

As seen in FIG. 6B, a slider 228b may include a body portion $228b_1$ and at least one arm $228b_2$ extending from body portion $228b_1$ and configured for slidable engagement in guide channels 130a, 130b (see FIG. 1) of electrosurgical pencil 100. Slider 228b includes a nub $228b_3$ extending or projecting from a bottom surface thereof, such as, for example, from a bottom surface of body portion $228b_1$. Slider 228b further includes a spring lever assembly having a stem $228b_4$ extending from body portion $228b_1$, on a side opposite nub $228b_3$, and defining a recess configured to retain a biasing member $228b_5$ therein. The spring lever assembly further includes a lever $228b_6$ pivotally connected to body portion $228b_1$ and having a tip $228b_7$ configured to extend over or overlie biasing member $228b_5$. The spring lever assembly is configured such that stem $228b_4$ is located distal or proximal of nub $228b_3$ and such that lever $228b_6$ extends away from nub $228b_3$.

In use, as slider 228b is moved distally and proximally relative to housing 102 of electrosurgical pencil 100, nub $228b_3$ moves along VDN 127 thereby affecting VDN 127 while tip $228b_7$ of lever $228b_6$ of the spring lever assembly inter-engages with detents or tactile features 131 formed in housing 102 of electrosurgical pencil 100 to thereby provide a degree of tactile feedback to the user of electrosurgical pencil 100. Biasing member $228b_5$ functions to maintain nub $228b_3$ in contact with VDN 127 and tip $228b_7$ of lever $228b_6$ of the spring lever assembly in contact with detents or tactile features 131 formed in housing 102 of electrosurgical pencil 100.

Figure 6C:
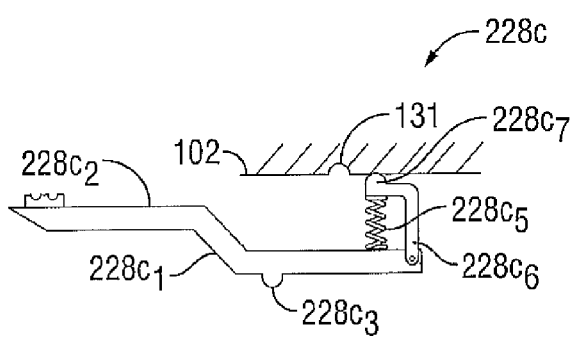
FIG. 6C is a schematic side elevational view of a slider according to yet another embodiment of the present disclosure, for use in an electrosurgical pencil as shown in FIGS. 1-4.

As seen in FIG. 6C, a slider $228c$ may include a body portion $228c_1$ and at least one arm $228c_2$ extending from body portion $228c_1$ and configured for slidable engagement in guide channels $130a$, $130b$ (see FIG. 1) of electrosurgical pencil 100. Slider $228c$ includes a nub $228c_3$ extending or projecting from a bottom surface thereof, such as, for example, from a bottom surface of body portion $228c_1$. Slider $228c$ further includes a spring lever assembly having a biasing member $228c_5$ supported on body portion $228c_1$, on a side opposite nub $228c_3$, and a lever $228c_6$ pivotally connected to body portion $228c_1$ and having a tip $228c_7$ configured to extend over or overlie biasing member $228c_5$. The spring lever assembly is configured such that biasing member $228c_5$ is located distal or proximal of nub $228c_3$ and such that lever $228c_6$ extends away from nub $228c_3$.

In use, as slider $228c$ is moved distally and proximally relative to housing 102 of electrosurgical pencil 100, nub $228c_3$ moves along VDN 127 thereby affecting VDN 127 while tip $228c_7$ of lever $228c_6$ of the spring lever assembly inter-engages with detents or tactile features 131 formed in housing 102 of electrosurgical pencil 100 to thereby provide a degree of tactile feedback to the user of electrosurgical pencil 100. Biasing member $228c_5$ functions to maintain nub $228c_3$ in contact with VDN 127 and tip $228c_7$ of lever $228c_6$ of the spring lever assembly in contact with detents or tactile features 131 formed in housing 102 of electrosurgical pencil 100.

In each of sliders $228a$-$228c$ shown in FIGS. 6A-6C and described above, it is contemplated that in some embodiments that actuator $228a_6$, or tips $228b_7$, $228c_7$ of levers $228b_6$, $228c_6$ may axially overlie respective nubs $228a_3$-$228c_3$. In this manner, the force of the biasing member $228a_5$-$228c_5$ acts directly in line with respective nubs $228a_3$-$228c_3$.

Figure 6D:
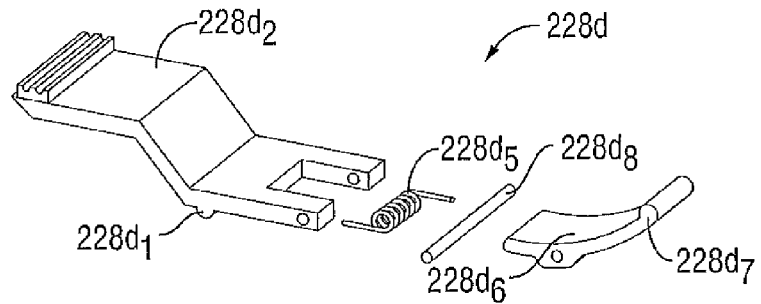
FIG. 6D is a schematic perspective view, with parts separated, of a slider according to a further embodiment of the present disclosure, for use in an electrosurgical pencil as shown in FIGS. 1-4.

Although the embodiment in FIGS. 6B-6C is shown to a use coil spring as the biasing member, it is contemplated that these slider designs may alternatively incorporate torsion springs of the type shown in FIG. 6D. As seen in FIG. 6D, a slider $228d$ may include a body portion $228d_1$ and at least one arm $228d_2$ extending from body portion $228d_1$ and configured for slidable engagement in guide channels $130a$, $130b$ (see FIG. 1) of electrosurgical pencil 100. Slider $228d$ includes a nub $228d_3$ extending or projecting from a bottom surface thereof, such as, for example, from a bottom surface of body portion $228d_1$. Slider $228d$ further includes a torsion spring lever assembly supported on body portion $228d_1$ having a biasing member $228d_5$ and a connector rod $228d_8$ pivotally connecting lever $228d_6$ to body portion $228d_1$ on a side adjacent nub $228d_3$. Lever $228d_6$ includes a tip $228d_7$ configured such that biasing member $228d_5$ is located distal or proximal of nub $228d_3$.

In use, as slider $228d$ is moved distally and proximally relative to housing 102 of electrosurgical pencil 100, nub $228d_3$ moves along VDN 127 thereby affecting VDN 127 while tip $228d_7$ of lever $228d_6$ of the spring lever assembly inter-engages with detents or tactile features 131 formed in housing 102 of electrosurgical pencil 100 to thereby provide a degree of tactile feedback to the user of electrosurgical pencil 100. Biasing member $228d_5$ functions to maintain nub $228d_3$ in contact with VDN 127 and tip $228d_7$ of lever $228d_6$ of the torsion spring lever assembly in contact with detents or tactile features 131 formed in housing 102 of electrosurgical pencil 100. One advantage to using a torsion spring lever assembly configuration as set forth in FIG. 6D is that such a configuration provides greater spring deflections with smaller spring constants, thus making the delivered force less sensitive to dimensional variations in slider $228d$.

Figure 7A:
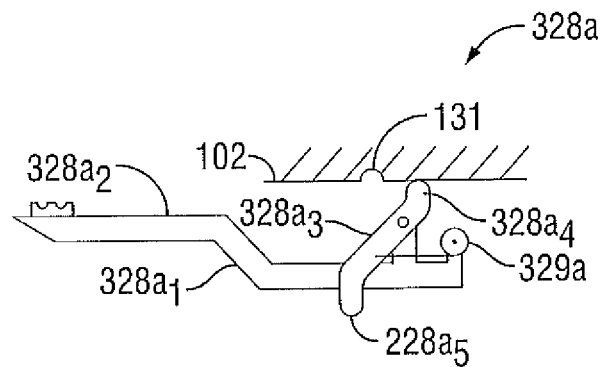
FIG. 7A is a schematic side elevational view of an alternate slider according to an embodiment of the present disclosure, for use in an electrosurgical pencil as shown in FIGS. 1-4.
Figure 7B:
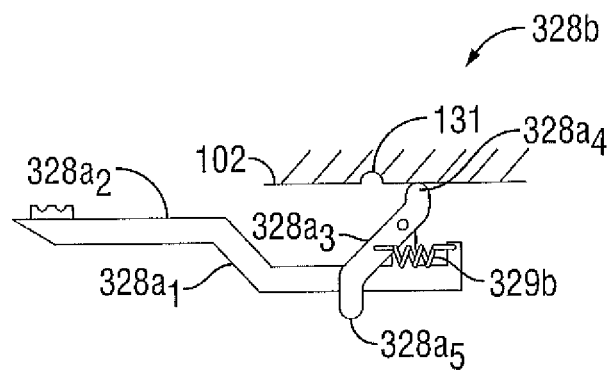
FIG. 7B is a schematic side elevational view of the alternate slider according to another embodiment of the present disclosure, for use in an electrosurgical pencil as shown in FIGS. 1-4.
Figure 7C:
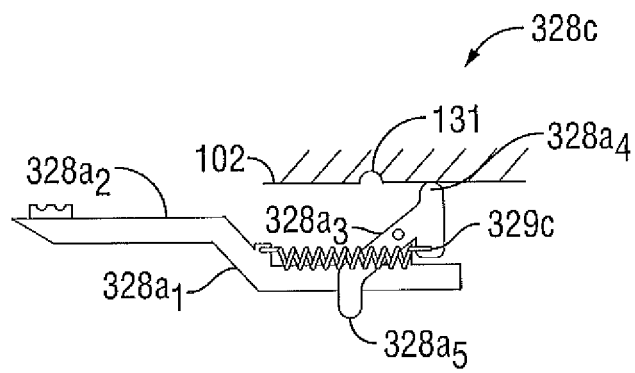
FIG. 7C is a schematic side elevational view of the alternate slider according to yet another embodiment of the present disclosure, for use in an electrosurgical pencil as shown in FIGS. 1-4.

Turning now to FIGS. 7A-7C, a series of sliders or intensity controllers 328 according to an embodiment of the present disclosure is shown. Sliders 328 are configured to increase a contact force exerted on VDN 127 while maintaining a degree of facility for an end user to move slider 328 relative to housing 102 of electrosurgical pencil 100.

As seen in FIGS. 7A-7C, a slider $328a$ may include a body portion $328a_1$ and at least one arm $328a_2$ extending from body portion $328a_1$ and configured for slidable engagement in guide channels $130a$, $130b$ (see FIG. 1) of electrosurgical pencil 100. Slider $328a$ includes a lever $328a_3$ pivotally connected to body portion $328a_1$. Lever $328a_3$ includes a first end $328a_4$ configured to extend above body portion $328a_1$ and a second end $328a_5$ configured to extend below body portion $328a_1$. First end $328a_4$ of lever $328a_3$ is configured to selectively engage detents or tactile features 131 formed in housing 102 of electrosurgical pencil 100 and second end $328a_5$ of lever $328a_3$ is configured to selectively engage VDN 127.

As seen in FIG. 7A, slider $328a$ may include a biasing member in the form of a coil or constant force spring $329a$, or as seen in FIG. 713 slider $328a$ may include a biasing member in the form of a tensile spring $329b$, or as seen in FIG. 7C slider $328a$ may include a biasing member in the form of a compression spring $329c$. Biasing members $329a$-$329c$ are each configured or arranged so as to maintain first end $328a_4$ of lever $328a_3$ in contact with or in engagement with detents or tactile features 131 formed in housing 102 of electrosurgical pencil 100 and to maintain second end $328a_5$ of lever $328a_3$ in engagement with VDN 127. Biasing members $329a$-$329c$ may be secured to and extend between a suitable location on lever $328a_3$ and a suitable location on body portion $328a_1$.

In use, as slider $328a$ is moved distally and proximally relative to housing 102 of electrosurgical pencil 100, first end $328a_4$ of lever $328a_3$ inter-engages with detents or tactile features 131 formed in housing 102 of electrosurgical pencil 100 to thereby provide a degree of tactile feedback to the user of electrosurgical pencil 100 while second end $328a_5$ of lever $328a_3$ moves along VDN 127 thereby affecting VDN 127. In particular, as first end $328a_4$ of lever $328a_3$ moves from one detent or tactile features 131 to an adjacent detent or tactile features 131, first end $328a_4$ of lever $328a_3$ is moved towards body portion $328a_1$ and second end $328a_5$ of lever $328a_3$ moves off of or reduces a pressure on VDN 127 and also is moved towards body portion $328a_1$. As first end $328a_4$ of lever $328a_3$ is moved into the adjacent detent or tactile features 131 second end $328a_5$ of lever $328a_3$ substantially strikes down onto, imparts or otherwise increases a pressure on VDN 127.

Figure 8A:
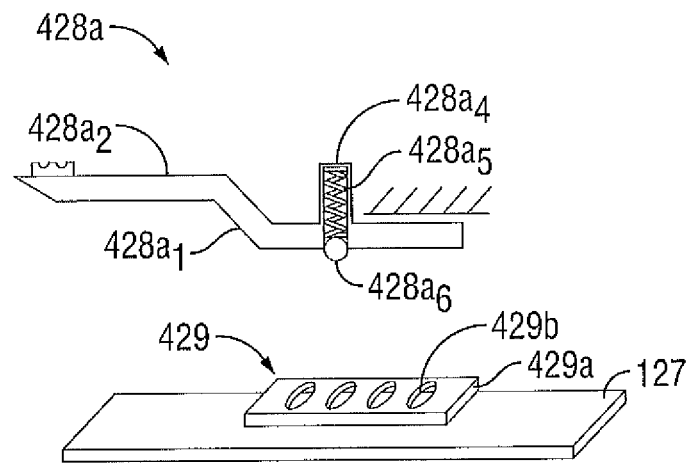
FIG. 8A is a schematic illustration of a further alternate slider and a tactile mask according to an embodiment of the present disclosure, for use in an electrosurgical pencil as shown in FIGS. 1-4.
Figure 8B:
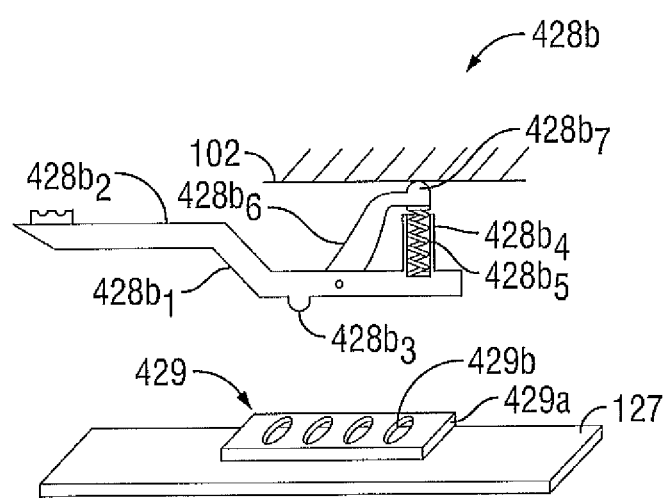
FIG. 8B is a schematic illustration of the further alternate slider according and a tactile mask to another embodiment of the present disclosure, for use in an electrosurgical pencil as shown in FIGS. 1-4.

Turning now to FIGS. 8A and 8B, a series of sliders or intensity controllers 428 and a tactile mask 429 according to an embodiment of the present disclosure are shown. Sliders 428 are configured to increase a contact force exerted on VDN 127 while maintaining a degree of facility for an end user to move slider 428 relative to housing 102 of electrosurgical pencil 100. Tactile mask 429 is configured to cause slider 428 to impact or strike against VDN 127.

As seen in FIG. 8A, a slider $428a$ may include a body portion $428a_1$ and at least one arm $428a_2$ extending from body portion $428a_1$ and configured for slidable engagement in guide channels $130a$, $130b$ (see FIG. 1) of electrosurgical pencil 100. Slider $428a$ includes a spring plunger assembly having a stem $428a_4$ extending from body portion $428a_1$ and defining a recess configured to retain a biasing member $428a_5$ and a tactile feedback transmitting feature in the form of an actuator $428a_6$ therein. The spring plunger assembly is configured such that actuator $428a_6$ extends from a bottom surface of body portion $428a_1$, in the direction of VDN 127.

Tactile mask 429 includes an elongate body portion 429a configured to overlie VDN 127. Body portion 429a defines a plurality of apertures or windows 429b formed therein along a length thereof. Tactile mask 429 is positioned over VDN 127 at a location such that apertures 429b may align or register with variable resistance elements 144d provided on lower layer 140b of VDN 127 (see FIG. 5).

In use, as slider 428a is moved distally and proximally relative to housing 102 of electrosurgical pencil 100, actuator $428a_6$ of spring plunger assembly moves over and between apertures 429b formed in tactile mask 429. In so doing, actuator $428a_6$ of spring plunger assembly impacts or strikes against VDN 127. Additionally, the inter-engagement of actuator $428a_6$ of spring plunger assembly with apertures 429b formed in tactile mask 429 provides a degree of tactile feedback to the user of electrosurgical pencil 100.

As seen in FIG. 8B, a slider 428b may include a body portion $428b_1$ and at least one arm $428b_2$ extending from body portion $428b_1$ and configured for slidable engagement in guide channels 130a, 130b (see FIG. 1) of electrosurgical pencil 100. Slider 428b includes a tactile feedback transmitting feature in the form of a nub $428b_3$ extending or projecting from a bottom surface thereof, such as, for example, from a bottom surface of body portion $428b_1$. Slider 428b further includes a spring lever assembly having a stem $428b_4$ extending from body portion $428b_1$, on a side opposite nub $428b_3$, and defining a recess configured to retain a biasing member $428b_5$ therein. The spring lever assembly further includes a lever $428b_6$ pivotally connected to body portion $428b_1$ and having a tip $428b_7$ configured to extend over or overlie biasing member $428b_5$. The spring lever assembly is configured such that stem $428b_4$ is located distal or proximal of nub $428b_3$ and such that lever $428b_6$ extends away from nub $428b_3$.

In use, as slider 428b is moved distally and proximally relative to housing 102 of electrosurgical pencil 100, nub $428b_3$ of slider 428b moves over and between apertures 429b formed in tactile mask 429. In so doing, nub $428b_3$ of slider 428b contacts VDN 127. Additionally, the inter-engagement of nub $428b_3$ of slider 428b with apertures 429b formed in tactile mask 429 provides a degree of tactile feedback to the user of electrosurgical pencil 100. Moreover, tip $428b_7$ of lever $428b_6$ rides against an inner surface of housing 102 of pencil 100 and biasing member $428b_5$ act on tip $428b_7$ of lever $428b_6$ to exert a force on body portion $428b_1$ and thereby press nub $428b_3$ of slider 428b against tactile mask 429.

Tactile mask 429 may be constructed from a rigid, semi-rigid or non-rigid material, from a resilient or non-resilient material, from a conductive or non-conductive material, from any combination thereof, or from any material suitable for the intended purpose of defining apertures and transmitting forces through said apertures.

Figure 9A:
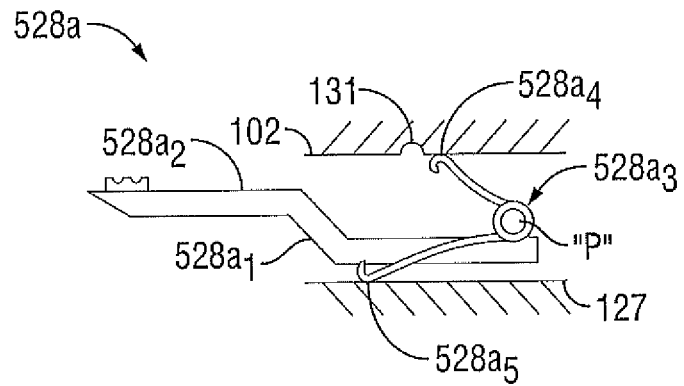
FIG. 9A is a schematic side elevational view of an alternate slider according to an embodiment of the present disclosure, for use in an electrosurgical pencil as shown in FIGS. 1-4.
Figure 9B:
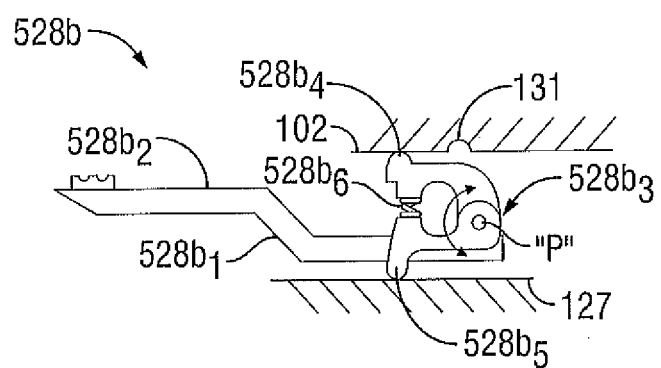
FIG. 9B is a schematic side elevational view of a further alternate slider according to another embodiment of the present disclosure, for use in an electrosurgical pencil as shown in FIGS. 1-4.

Turning now to FIGS. 9A and 9B, a series of sliders or intensity controllers 528 according to an embodiment of the present disclosure is shown. Sliders 528 are configured to increase a contact force exerted on VDN 127 while maintaining a degree of facility for an end user to move slider 528 relative to housing 102 of electrosurgical pencil 100.

As seen in FIG. 9A, a slider 528a may include a body portion $528a_1$ and at least one arm $528a_2$ extending from body portion $528a_1$ and configured for slidable engagement in guide channels 130a, 130b (see FIG. 1) of electrosurgical pencil 100. Slider 528a includes a biasing member, in the form of a torsion spring $528a_3$ pivotally supported on body portion $528a_1$ at pivot point "P". Torsion spring $528a_3$ includes a first leg $528a_4$ extending from pivot point "P" and configured to engage a surface of housing 102 of electrosurgical pencil 100, and a second leg $528a_5$ extending from pivot point "P" and configured to engage VDN 127. As seen in FIG. 9A, first leg $528a_4$ of torsion spring $528a_3$ extends above body portion $528a_1$ and second leg $528a_5$ of torsion spring $528a_3$ extends below body portion $528a_1$.

In use, as slider 528a is moved distally and proximally relative to housing 102 of electrosurgical pencil 100, second leg $528a_5$ of torsion spring $528a_3$ moves along VDN 127 thereby affecting VDN 127 while first leg $528a_4$ of torsion spring $528a_3$ inter-engages with detents or tactile features 131 formed in housing 102 of electrosurgical pencil 100 to thereby provide a degree of tactile feedback to the user of electrosurgical pencil 100. As first leg $528a_4$ of torsion spring $528a_3$ is flexed downwardly, in the direction of body portion $528a_1$, as slider 528a is moved distally and proximally relative to housing 102 of electrosurgical pencil 100, second leg $528a_5$ of torsion spring $528a_3$ is pressed more or less into the surface of VDN 127.

As seen in FIG. 9B, a slider 528b may include a body portion $528b_1$ and at least one arm $528b_2$ extending from body portion $528b_1$ and configured for slidable engagement in guide channels 130a, 130b (see FIG. 1) of electrosurgical pencil 100. Slider 528b includes a link assembly $528b_3$ pivotally supported on body portion $528b_1$ at pivot point "P". Link assembly $528b_3$ includes a first leg $528b_4$ extending from pivot point "P" and configured to engage a surface of housing 102 of electrosurgical pencil 100, a second leg $528b_5$ extending from pivot point "P" and configured to engage VDN 127, and a biasing member $528b_6$ interposed between first leg $528b_4$ a second leg $528b_5$. As seen in FIG. 9B, first leg $528b_4$ of link assembly $528b_3$ is in registration with or extends above second leg $528b_5$ of link assembly $528b_3$.

In use, as slider 528b is moved distally and proximally relative to housing 102 of electrosurgical pencil 100, second leg $528b_5$ of link assembly $528b_3$ moves along VDN 127 thereby affecting VDN 127 while first leg $528b_4$ of link assembly $528b_3$ inter-engages with detents or tactile features 131 formed in housing 102 of electrosurgical pencil 100 to thereby provide a degree of tactile feedback to the user of electrosurgical pencil 100. As first leg $528b_4$ of link assembly $528b_3$ is moved downwardly, in the direction of body portion $528b_1$, as slider 528b is moved distally and proximally relative to housing 102 of electrosurgical pencil 100, biasing member $528b_6$ transmits forces to second leg $528b_5$ of link assembly $528b_3$ to press more or less into the surface of VDN 127.

Although the subject apparatus has been described with respect to preferred embodiments, it will be readily apparent, to those having ordinary skill in the art to which it appertains, that changes and modifications may be made thereto without departing from the spirit or scope of the subject apparatus.

What is claimed is:

1. An electrosurgical pencil, comprising:
    a housing configured to support an electrocautery electrode;
    at least one voltage divider network supported on the housing, the at least one voltage divider network operable to electrically connect to a source of electrosurgical energy for controlling at least one of an intensity and a mode of electrosurgical energy being delivered to the electrocautery electrode; and
    an intensity controller slidably supported on the housing, wherein the intensity controller is configured to exert a force on the at least one voltage divider network and provide a tactile feedback to a user of the electrosurgical pencil as the intensity controller is moved relative to the housing, wherein the intensity controller includes a lever pivotally connected to a body portion thereof, the lever having a proximal end and a distal end, the proximal end having a proximal tip engaging the housing and the at least one voltage divider network, the proximal tip of the lever further engaging one end of a biasing member, the biasing member, in its entirety, orthogonally disposed with respect to the housing, and orthogonally disposed, in its entirety, directly beneath the proximal tip of the lever, such that the biasing member is coaxially displaced, in its entirety, with the proximal tip, when the proximal tip engages a tactile feature formed in the housing.

2. The electrosurgical pencil according to claim 1, wherein the biasing member is enclosed within a structure.

3. The electrosurgical pencil according to claim 1, wherein the biasing member is configured to maintain the proximal tip of the lever in contact with the tactile feature formed in the housing.

4. The electrosurgical pencil according to claim 1, wherein the biasing member is one of a coil spring, a tension spring and a compression spring.

5. The electrosurgical pencil according to claim 1, wherein the tactile feature includes one or more adjacent detents.

6. The electrosurgical pencil according to claim 5, wherein movement of the proximal tip of the lever into the one or more adjacent detents causes the distal end of the lever to strike the at least one voltage divider network.

7. An electrosurgical device configured for connection to a source of electrosurgical energy, the electrosurgical device comprising:

a housing;

an electrical circuit supported within the housing, the electrical circuit being connectable to the source of electrosurgical energy; and a controller slidably supported on the housing, wherein the controller is configured to exert a force on the electrical circuit to affect a change in the electrical circuit and to exert a force on a surface of the housing to provide a tactile feedback to a user of the electrosurgical device as the controller is moved relative to the housing, wherein the controller includes a lever pivotally connected to a body portion thereof, the lever having a proximal end and a distal end, the proximal end having a proximal tip engaging the housing and the electrical circuit, the proximal tip of the lever further engaging one end of a biasing member, the biasing member, in its entirety, orthogonally disposed with respect to the housing, and orthogonally disposed, in its entirety, directly beneath the proximal tip of the lever, such that the biasing member is coaxially displaced, in its entirety, with the proximal tip, when the proximal tip engages a tactile feature formed in the housing.

8. The electrosurgical device according to claim 7, wherein the electrical circuit comprises at least one voltage divider network capable of controlling at least one of an intensity and a mode of electrosurgical energy being delivered.

9. The electrosurgical device according to claim 7, wherein the biasing member is enclosed within a structure.

10. The electrosurgical device according to claim 7, wherein the biasing member is configured to maintain the proximal tip of the lever in contact with the tactile feature formed in the housing.

11. The electrosurgical device according to claim 7, wherein the member is one of a coil spring, a tension spring and a compression spring.

12. The electrosurgical device according to claim 7, wherein the tactile feature includes one or more adjacent detents.

13. The electrosurgical device according to claim 12, wherein movement of the proximal tip of the lever into the one or more adjacent detents causes the distal end of the lever to strike the at least one voltage divider network.

* * * * *